US006950690B1

(12) United States Patent
Meron et al.

(10) Patent No.: US 6,950,690 B1
(45) Date of Patent: Sep. 27, 2005

(54) METHOD FOR DELIVERING A DEVICE TO A TARGET LOCATION

(75) Inventors: Gavriel Meron, Petach Tikva (IL); Gavriel J. Iddan, Haifa (IL)

(73) Assignee: Given Imaging LTD, Yoqneam (IL)

( * ) Notice: Subject to any disclaimer, the term of this patent is extended or adjusted under 35 U.S.C. 154(b) by 0 days.

(21) Appl. No.: 09/807,892

(22) PCT Filed: Oct. 21, 1999

(86) PCT No.: PCT/IL99/00554

§ 371 (c)(1),
(2), (4) Date: Jun. 6, 2001

(87) PCT Pub. No.: WO00/22975

PCT Pub. Date: Apr. 27, 2000

(30) Foreign Application Priority Data

Oct. 22, 1998 (IL) .................................. 126727

(51) Int. Cl.⁷ .............................................. A61B 5/05
(52) U.S. Cl. ...................... 600/424; 128/922; 382/128; 382/133; 600/117
(58) Field of Search ................... 600/407, 473, 600/476, 424, 425, 427, 109, 111, 117, 118; 128/903, 899, 922; 604/890.1, 891.1, 892.1, 604/93.01; 382/128, 133

(56) References Cited

U.S. PATENT DOCUMENTS

| | | |
|---|---|---|
| 3,971,362 A | 7/1976 | Pope et al. |
| 4,239,040 A | 12/1980 | Hosoya et al. |
| 4,278,077 A | 7/1981 | Mizumoto |
| 4,439,197 A | 3/1984 | Honda et al. |
| 4,689,621 A | 8/1987 | Kleinberg |
| 4,803,992 A | 2/1989 | Lemelson |
| 4,844,076 A | 7/1989 | Lesho et al. |
| 5,042,486 A | 8/1991 | Pfeiler et al. |
| 5,081,041 A | 1/1992 | Yafuso et al. |
| 5,109,870 A | 5/1992 | Silny et al. |
| 5,211,165 A | 5/1993 | Dumoulin et al. |
| 5,279,607 A | 1/1994 | Schentag et al. |
| 5,330,427 A | 7/1994 | Weissenburger |
| 5,395,366 A | 3/1995 | D'Andrea et al. |
| 5,429,132 A | 7/1995 | Guy et al. |
| 5,479,935 A | 1/1996 | Essen-Moller |
| 5,558,640 A | 9/1996 | Pfeiler et al. |

(Continued)

FOREIGN PATENT DOCUMENTS

DE    34 40 177    5/1986

(Continued)

OTHER PUBLICATIONS

The Radio Pill, Rowlands, et al., British Communications and Electronics, Aug. 1960, pp. 598-601.

(Continued)

*Primary Examiner*—Eleni Mantis Mercader
(74) *Attorney, Agent, or Firm*—Pearl Cohen Zedek Latzer, LLP (57) ABSTRACT

Capsule (60) moves through the gastrointestinal tract (62) in a first pass to generate a map of the gastrointestinal tract, and to identify a location of interest. In its second pass, capsule (60) moves through the gastrointestinal tract, and is controlled to perform a job at the identified location. Repeated localizations generate generate a map of the route taken by the capsule in the gastrointestinal tract (62). images displayed on the image monitor (61) are compared with the generated map displayed on the position monitor (63) to identify the location of a pathology (72).

8 Claims, 5 Drawing Sheets

U.S. PATENT DOCUMENTS

| | | | |
|---|---|---|---|
| 5,604,531 A | 2/1997 | Iddan et al. | |
| 5,800,350 A | 9/1998 | Coppelson et al. | |
| 5,819,736 A | 10/1998 | Avny et al. | |
| 5,833,603 A | 11/1998 | Kovacs et al. | |
| 5,837,196 A | 11/1998 | Pinkel et al. | |
| 5,913,820 A | 6/1999 | Bladen et al. | |
| 5,993,378 A | 11/1999 | Lemelson | |
| 6,099,482 A | 8/2000 | Brune et al. | |
| 6,149,581 A | 11/2000 | Klingenstein | |
| 6,240,312 B1 * | 5/2001 | Alfano et al. | 600/476 |
| 6,285,897 B1 | 9/2001 | Kilcoyne et al. | |
| 6,324,418 B1 * | 11/2001 | Crowley et al. | 600/476 |
| 6,369,812 B1 * | 4/2002 | Iyriboz et al. | 345/419 |
| 6,395,562 B1 | 5/2002 | Hammock et al. | |
| 6,475,145 B1 | 11/2002 | Baylor | |
| 6,488,694 B1 | 12/2002 | Lau et al. | |
| 2001/0035902 A1 | 11/2001 | Iddan, et al. | |
| 2002/0001695 A1 | 1/2002 | Tajima et al. | |
| 2002/0015952 A1 | 2/2002 | Anderson et al. | |
| 2002/0103417 A1 | 8/2002 | Gazdzinski | |
| 2002/0173718 A1 | 11/2002 | Frisch et al. | |
| 2002/0177779 A1 | 11/2002 | Adler et al. | |
| 2002/0198439 A1 | 12/2002 | Mizuno | |
| 2003/0020810 A1 | 1/2003 | Takizawa et al. | |
| 2003/0023150 A1 | 1/2003 | Yokoi et al. | |

FOREIGN PATENT DOCUMENTS

| | | |
|---|---|---|
| FR | 2688997 | 10/1993 |
| JP | 4109927 | 4/1992 |
| JP | 5015515 | 1/1993 |
| JP | 6285044 | 4/1993 |
| JP | 7111985 | 5/1995 |
| JP | 2002010990 | 1/2002 |
| WO | WO 99/32028 | 7/1999 |
| WO | WO 00/22975 | 4/2000 |
| WO | WO 01/08548 | 2/2001 |
| WO | WO 02/55984 | 7/2002 |

OTHER PUBLICATIONS

Wellesley company sends body montiors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

"Video Camera to "TAKE""—RF System Lab, Dec. 25, 2001.

"Heidelberger Kapsel—ein Kleinstsender fur die pH-Messung im Magen", Lange, et al., Telefunken-Zeitung, Jg 36 (1963) Heft 5, pp. 265-270.

"New smart plastic has good memory"—Turke, 2001.

Heidelberger Kapsel—ein Kleinstsender fur die pH-Messung im Magen, Lange, et al., Telefunken-Zeitung, Jg 36 (1963) Heft 5, pp. 265-270.

Supplementary Partial European Search Report, Mar. 19, 2004.

* cited by examiner

METHOD FOR DELIVERING A DEVICE TO A TARGET LOCATION

PRIOR APPLICATION INFORMATION

The present application claims benefit from the International Application Number PCT/IL99/00554 filed 21 Oct. 1999 and entitled "A METHOD FOR DELIVERING A DEVICE TO TARGET LOCATION", which in turn claims priority from Israeli Application 12727, filed on 22 Oct. 1998.

FIELD OF THE INVENTION

The present invention relates to a method for identifying a target location in the gastrointestinal tract and for direct delivery of a device to the identified location.

BACKGROUND OF THE INVENTION

In the gastrointestinal tract, the stomach is connected, through the small intestine, a long tube that folds many times to fit inside the abdomen, to the large intestine. There are numerous pathologies of the gastrointestinal tract, such as lesions causing chronic gastrointestinal tract blood loss, which occurs in about 2% of US adults, malignancies, most of which give a poor prognosis, and bowel obstructions; simple, closed-loop, strangulated and incarcerated. Some of these pathologies, such as small intestinal tumors, are difficult to diagnose. Diagnostic methods of the small intestine are usually symptom related or invasive, such as barium enemas or surgery. New methods of diagnosis can lead to an earlier diagnosis and improved prognosis.

Figure 1:
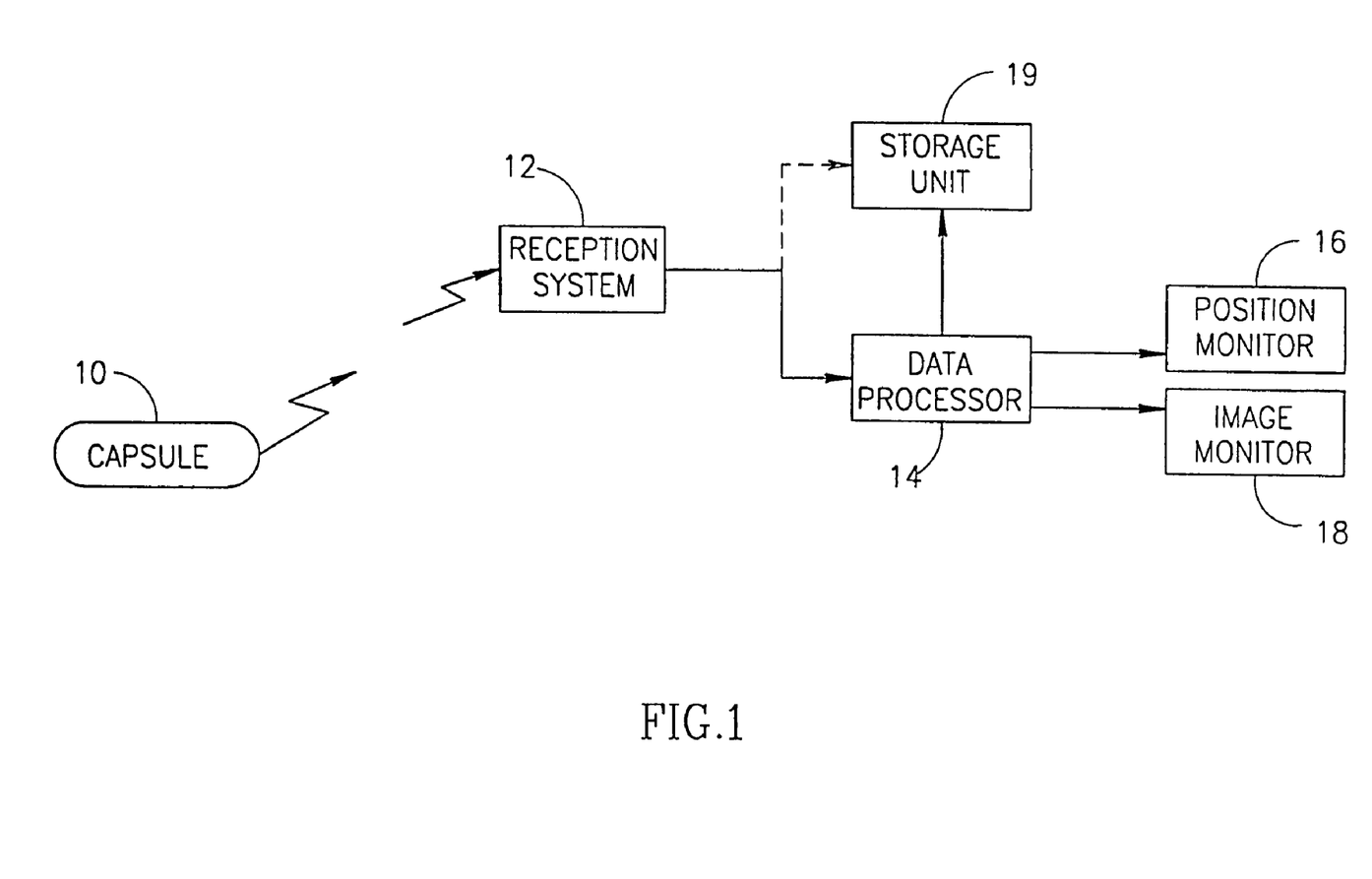
FIG. 1 is a block diagram illustration of a prior art in vivo video camera system for imaging the gastrointestinal tract.

U.S. Pat. No. 5,604,531 describes an in vivo video camera system which can image the gastrointestinal tract. Reference is now made to FIG. 1, which is a block diagram illustration of a prior art in vivo video camera system for imaging the gastrointestinal tract. The in vivo video camera system typically comprises a swallowable capsule 10 for viewing inside the digestive system and for transmitting video data, a reception system 12 typically located outside a patient, and a data processor 14 for processing the video data. The data processor 14 typically operates two monitors, a position monitor 16 on which the current location of the capsule 10 within the digestive system is displayed and an image monitor 18 on which the image currently viewed by the capsule 10 is displayed.

The reception system 12 can either be portable, in which case, the data it receives is temporarily stored in a storage unit 19, prior to its processing in data processor 14, or it can be stationary and close to the data processor 14.

Figure 2:
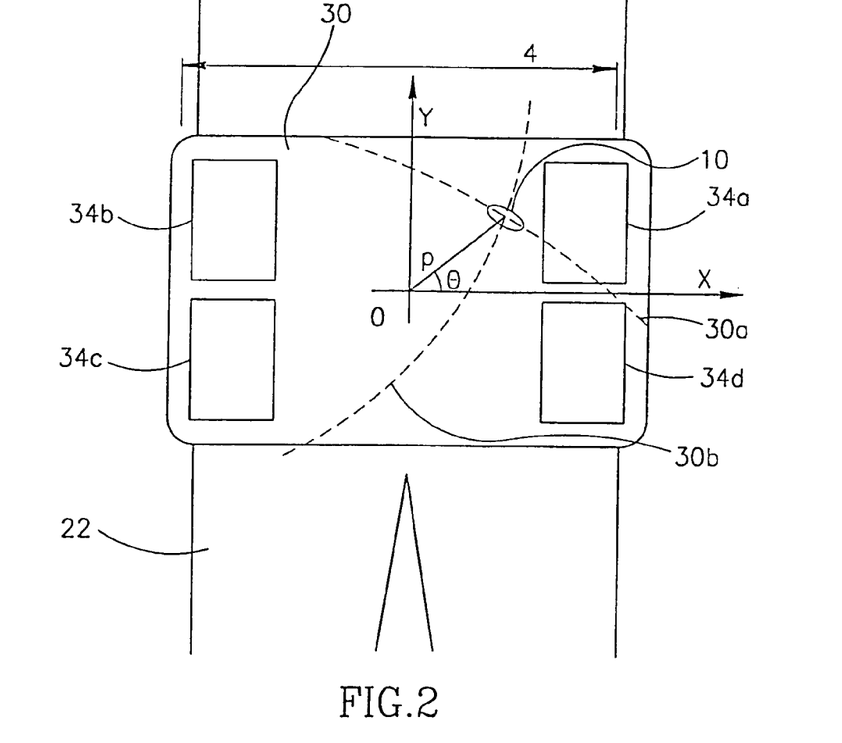
FIG. 3 is a top view illustration of the antenna array and FIG. 2 is a cross-sectional illustration of the antenna array.
Figure 3:
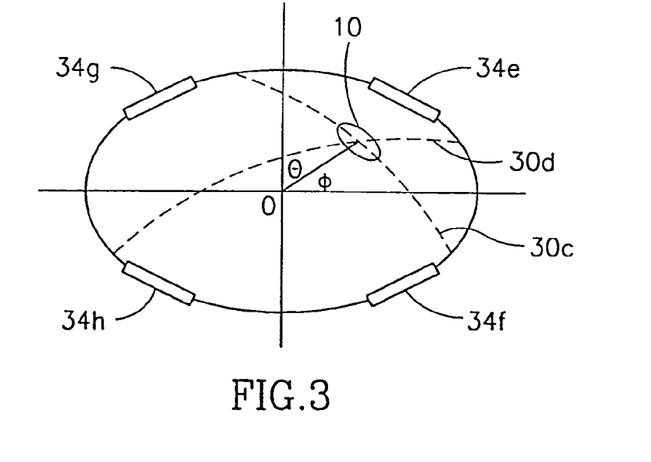

Reference is now made to FIGS. 2 and 3 which are a schematic illustration of calculations performed by a prior art data processor for processing the video data obtained by the above in vivo video camera system. FIG. 2 is a front view illustration of the patient 22 with an antenna array 30 wrapped around him. On it, four antennas 34a–34d are noted. Antennas 34a and 34b are located in a column at one side of the patient 22 and antennas 34c and 34d are located in a column at the other side of the patient 22.

Since the strength of a signal received by any given antenna depends on its distance from and angle to the transmitter, the ratio of the signal strengths between any two antennas, which have the transmitter between them, is constant along a curve which intersects the location of the transmitter. Thus, antennas 34a and 34b define curve 30a and antennas 34c and 34d define curve 30b.

The intersection of curves 30a and 30b is the location of the transmitter which is the location of the capsule 10. The curves 30a and 30b are typically determined in a calibration step for a pre defined number of constant values.

The designation of antennas 34a–34d depends on and is determined from the width $L_1$ of the patient 22, which value is typically provided to data processor 14 (of FIG. 1). Alternatively, there can be a plurality of antenna arrays 30, one for each of a pre-defined number of widths $L_1$. The antennas 34a–34d are then constant for each antenna array 30.

The location of the capsule 10, thus generated, is typically denoted by a two-dimensional vector P, having a length P and an angle □, from the center point O of an X-Y coordinate system.

The cross-sectional location (within an X-Z plane) of the capsule 10 can also be determined using a similar calculation to that illustrated in FIG. 2. A cross-section of the patient 22 is illustrated in FIG. 3. For this determination, four antennas 34e–34h, which are opposite in a cross-sectional manner, are utilized.

Once again, the ratio of the signal strengths between two antennas, which have the transmitter between them, is constant along a curve which intersects the location of the transmitter. Thus, antennas 34e and 34h define curve 30c and antennas 34f and 34g define curve 30d.

The location of the capsule 10 thus generated is typically denoted by a two-dimensional vector Q having a length Q and an angle □, from the center point O.

The two vectors P and Q are combined to determine the three-dimensional location of the capsule 10. The location can be displayed two- or three-dimensionally on position monitor 16 (of FIG. 1), typically, though not necessarily, as an overlay to a drawing of the digestive tract.

There exist methods for the delivery of medicament to a selected site in the gastrointestinal tract, such as the use of time delivery capsules made of material that dissolves in a particular environment and/or within a particular time period, within the gastrointestinal tract. In these methods, the delivery of medicament is dependent on the predictability of the particular environment to which the capsule is directed.

Controllable apparatuses for delivery of medicaments are described in U.S. Pat. Nos. 5,558,640 and 4,239,040. While using these apparatuses or capsules the delivery of medicament may be obstructed, such as by folds in the intestine.

These methods can not be relied upon for localized release of a medicament.

U.S. Pat. No. 5,279,607 describes a method of obtaining directional data from the passage of an ingestible radio signal transmitting capsule. This data is subsequently compared to directional data from a capsule carrying medicament passing through the alimentary canal, for remotely triggering the release of medicament at a calculated geometric location along the gastrointestinal tract. A location selected in this method, cannot be aligned with sites of interest, such as pathologies, since no diagnostic information, such as information relating to the pathology, can be obtained in this method. Furthermore, due to the constant peristaltic movement of the alimentary canal, the geometric location of a site is not the same in a first and second pass, so that this one parameter is only partially sufficient for selection of a site.

There exist no medicament delivering systems which combine diagnostic and therapeutic processes.

SUMMARY OF THE INVENTION

It is an object of the present invention to provide a method for delivering a utility device to a target location in the gastrointestinal tract. The method combines identification of a target in the gastrointestinal tract and delivery of a utility device to the identified target location. The method of the present invention comprises the steps of:

a) generating a map of the gastrointestinal tract, employing a sensing and utility device for a first pass, or, optionally, a plurality of passes through the gastrointestinal tract; and b) delivering the sensing and utility device to a target location identified on the map, using the sensing and utility device in a second pass or, optionally, a plurality of passes, through the gastrointestinal tract. The sensing and utility device used in the second pass, may be the same or different than the device used in the first pass.

The term "sensing and utility device", in the present invention, refers to a device which is swallowable or placeable (such as described in IL patent application number 122716, assigned to the common assignees of the present invention and which is hereby incorporated by reference), and is capable of sensing selected parameters of the gastrointestinal tract. The device also comprises means for performing a job in the gastrointestinal tract. It is controllable and is capable of being monitored and of generating a map of the gastrointestinal tract.

The sensing and utility device may comprise, for example, any one or any combination of a video camera, which generates an image of the gastrointestinal tract, or sensing means, such as temperature, pressure or pH sensors or means for sensing the presence of blood, microorganisms, parasites or pathological indications or any objects alien to the gastrointestinal tract.

Means for performing a job may be any means suitable for researching, diagnosing or treating pathologies in the gastrointestinal tract, for example, fluid or cell sampling means, marker releasing means or medicament releasing means.

A map of the gastrointestinal tract may be generated by inserting the sensing and utility device into the gastrointestinal tract, monitoring the progress of the device through the gastrointestinal tract and optionally displaying the locations, two or three dimensionally, on a position monitor.

Monitoring the device is by periodically or repeatedly locating the device, preferably, as described in U.S. Pat. No. 5,604,531 assigned to the common assignees of the present invention. U.S. Pat. No. 5,604,531 is hereby incorporated by reference.

Delivering the sensing and utility device to a target location identified on the map comprises the steps of inserting the sensing and utility device into the gastrointestinal tract, in a second pass, receiving data from the device, either visual, from a video camera, or from the output of other sensing means, performing signal analysis of the data generated in the first pass and the data received from said sensing and utility device in the second pass; and controlling, such as by IR or telephony, the sensing and utility device according to the signal analysis.

The method of the present invention may be used for research, diagnostic or therapeutic purposes in the gastrointestinal tract.

BRIEF DESCRIPTION OF THE FIGURES

The present invention will be understood and appreciated more fully from the following detailed description taken in conjunction with the drawings in which:

FIGS. 2 and 3 are schematic illustrations of calculations performed by a prior art data processor for processing the video data obtained by the in vivo video camera system for imaging the gastrointestinal tract, utilizing an antenna array, wherein

DETAILED DESCRIPTION OF THE INVENTION

The method of the present invention combines diagnostic and therapeutic processes. For example, the method combines identifying and localizing a pathology in the gastrointestinal tract with administrating treatment to the location of the pathology, by non invasive means. This combination is provided by employing a sensing and utility device which is inserted into the gastrointestinal tract, either by swallowing it or by placing it in the gastrointestinal tract. The above mentioned IL patent application 122716 describes a device for the placement of an autonomous capsule in the gastrointestinal tract, which bypasses the need for swallowing the capsule by the patient.

Figure 4:
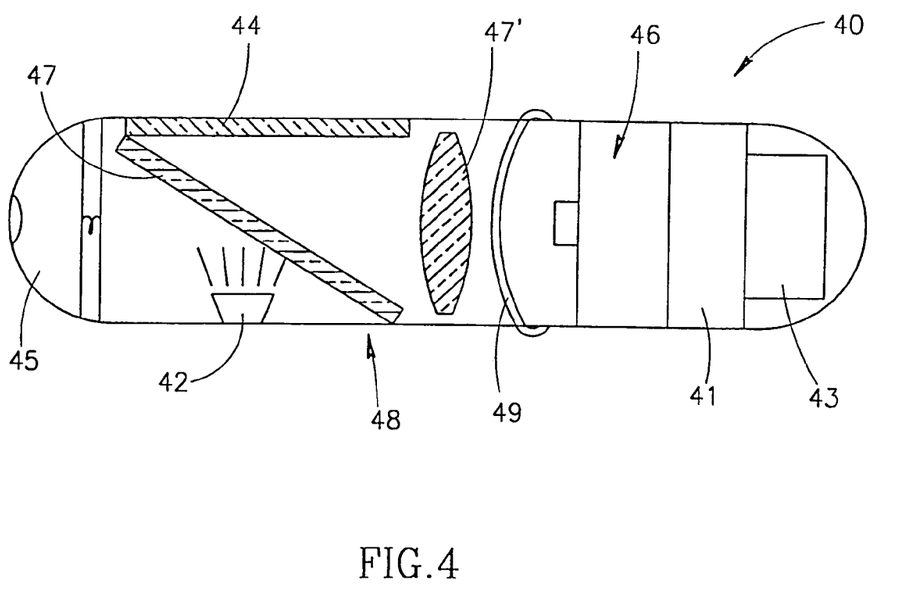
FIG. 4 is an illustration of a sensing and utility device according to a preferred embodiment of the invention.

Reference is now made to FIG. 4 which is an illustration of a sensing and utility device according to a preferred embodiment of the invention. The sensing and utility capsule shaped device, generally referenced 40, typically comprises a light source 42, a viewing window 44, through which the light illuminates the inner portions of the digestive system, a camera system 46, such as a charge-coupled device (CCD) or CMOS camera, which detects the images, an optical system 48 (typically comprising a mirror 47 and a focusing lens 47') which focuses the images onto the CCD or CMOS camera system 46, a transmitter 41, which transmits the video signal of the CCD or CMOS camera system 46, a power source 43, such as a battery, which provides power to the entirety of electrical elements of the capsule and a storage compartment 45, for the controllable discharge of medicaments or markers or for the controllable collection of fluid or cell samples from the environment, such as in a biopsy procedure.

The sensing and utility device can additionally include any known sensor element 49 such as temperature, pressure or pH sensors or means for sensing the presence of blood, microorganisms, parasites or pathological indications or any objects alien to the gastrointestinal tract.

Figure 5A:
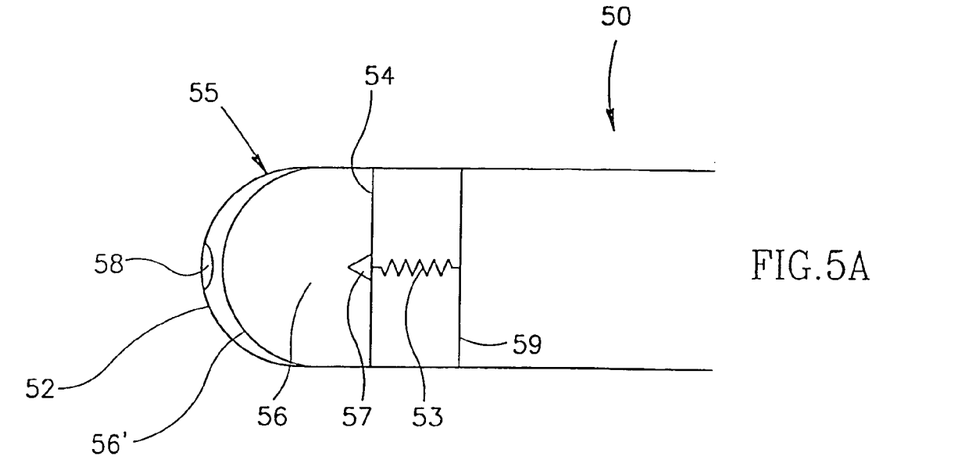
FIG. 5A is an illustration of a storage compartment, according to a preferred embodiment of the invention, in a recoiled-position of the bi stable spring.
Figure 5B:
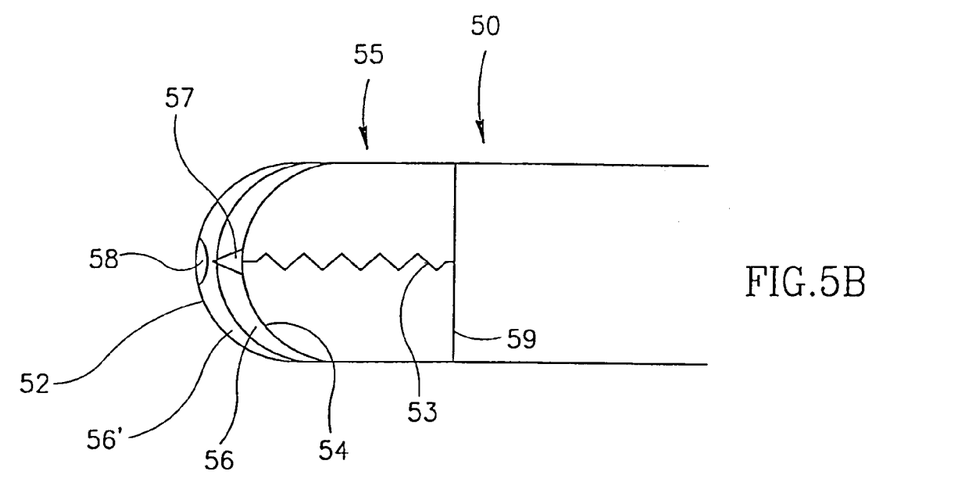
FIG. 5B is an illustration of a storage compartment, according to a preferred embodiment of the invention, in an extended position of the bi stable spring.
Figure 5C:
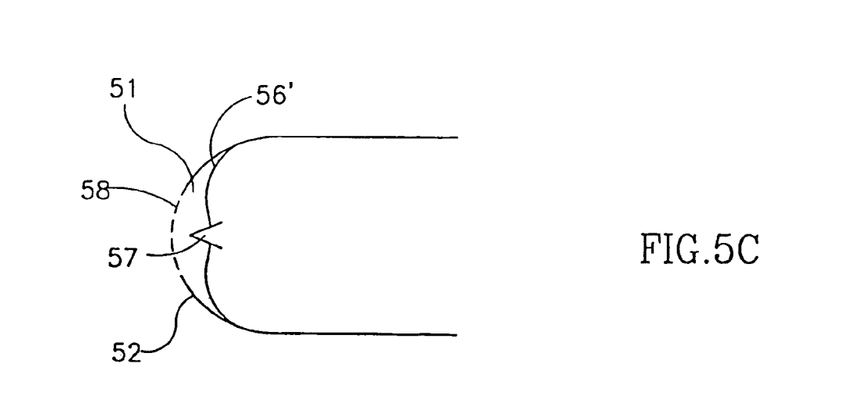
FIG. 5C is an enalrgement of the storgae compartment tip, according to a preferred embodiment of the invention.

Reference is now made to FIGS. 5A, 5B and 5C which are illustrations of a storage compartment, according to a preferred embodiment of the invention.

Storage compartment 55 is located preferably at an end of the sensing and utility device, generally referenced 50. The storage compartment is defined by an inflexible barrier 59 and the device shell. The storage compartment contains a pouch 56 made of flexible material which is encased by the device outer shell 52 and by a firm diaphragm 54 having an elasticity which will allow it to accommodate to a capsule shape. Diaphragm 54 is horizontally movable between the inflexible barrier 59 and the device tip. At the device tip there is an area 58, in the outer shell of the device, which is permeable and which allows passage of substances from or into the pouch 56. Permeability may be conferred, for instance by the area 58 being porous or sieve like. The pouch 56 is designed to retain substances such as releasable medicaments or markers or such as fluid or cell samples from the gastrointestinal tract environment. The pouch 56 bulk is determined by a bi stable spring 53, preferably made of a memory shape metal such as TiNi. The spring 53 is attached, at one end to the solid barrier 59, and at its other end, to the diaphragm 54. The spring 53 may be made to extend (as shown in FIG. 5B) or recoil (as shown in FIG. 5A) by providing different temperatures, as known in the art (the means for providing different temperatures, such as conducting wires, are not shown). Thus, the pouch 56 bulk may be reversably increased or decreased.

FIG. 5A illustrates a piercing pin 57 which is attached to the pouch wall and which protrudes into the pouch 56 inner space, in the direction of the opposing pouch wall 56'. For releasing a substance from pouch 56 into the gastroinestinal tract environment, spring 53 is made to extend, causing diaphragm 54 to move towards the device end, thrusting the peircing pin 57 into the opposing pouch wall 56', rupturing it. A substance contained in the pouch 56 will be released into a space 51 provided between the opposing pouch wall 56' and the outer shell permeable area 58. The released substance may then pass through the openings in the permeable area 58 into the gastrointestinal tract.

FIG. 5B illustrates a pouch 56 meant for collecting a sample from the gastrointestinal tract. In this embodiment the bi stable spring 53 is lodged in opposing pouch wall 56'. The spring 53 is made to recoil, pulling with it diaphragm 54 and piercing pin 57, such that piercing pin 57 is dislodged from the opposing pouch wall 56', rupturing it and leaving an opening in the pouch, through which substances from the environment are drawn into the pouch 56. The opening in the pouch is sealed after the sample is drawn in from the environment, ensuring a fixed volume and sterility of the collected sample.

Pin 57 may be a hollow cylinder through which substances may pass to or from the gastrointestinal tract.

FIG. 5C is an enlargement of the device end, through which substances are drawn into, or released from, the pouch. As can be seen in this figure, space 51 is provided, ensuring that the pin 57, either before being dislodged from wall 56' for collecting substances, or when piercing wall 56' for release of substances, doesn't protrude further than the device shell 52 and injure the patient's insides.

Figure 6:
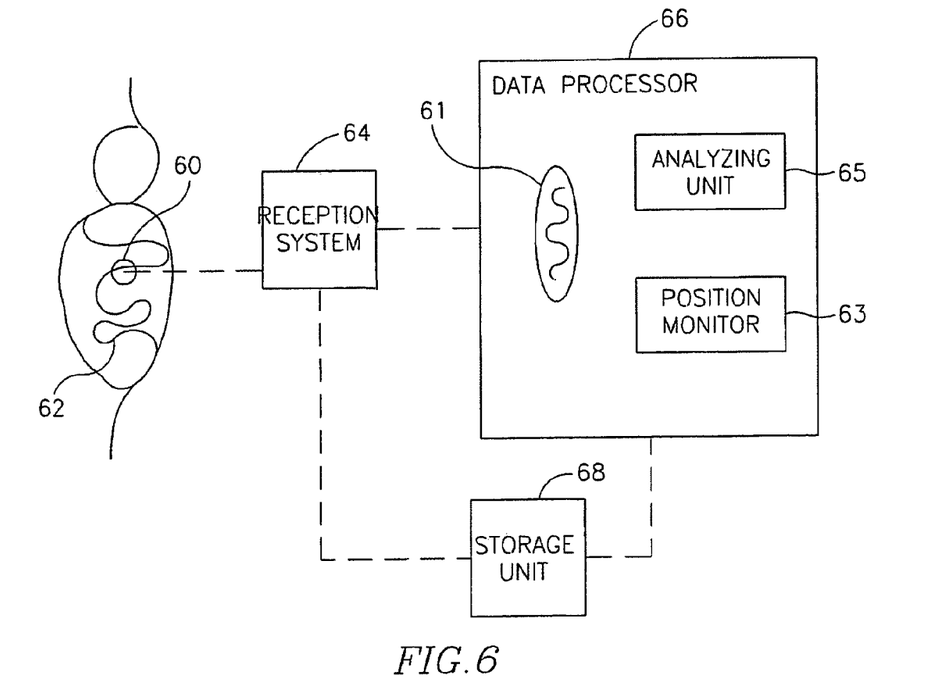
FIG. 6 is an illustration of a sensing and utility device operable according to a preferred embodiment of the invention.
Figure 7:
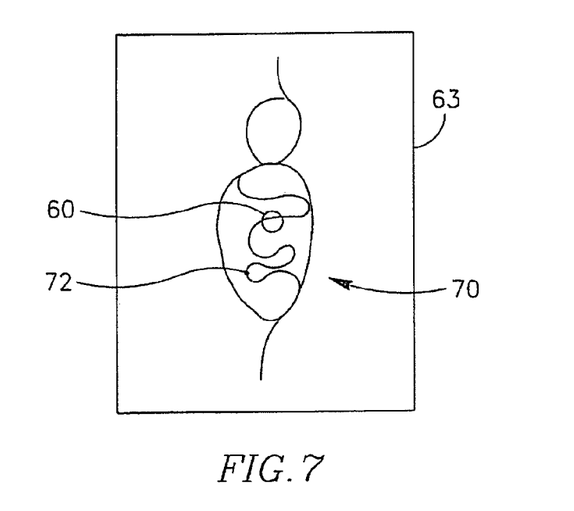
FIG. 7 is an illustration of a generated and displayed map in the method according to a preferred embodiment of the invention.

Reference is now made to FIGS. 6 and 7. FIG. 6 is an illustration of a sensing and utility device operable according to a preferred embodiment of the invention, and FIG. 7 is an illustration of a map of the gastrointestinal tract generated in the method, according to a preferred embodiment of the invention.

Capsule 60 moves through the gastrointestinal tract 62 in a first pass to generate, by visual means, a map of the gastrointestinal tract and to identify, by visual means or other sensor means, a location of interest in the gastrointestinal tract. In its second pass, capsule 60 moves through the gastrointestinal tract and is controlled to perform a job at the identified location.

Recognition of the location, identified in the first pass, is done in analyzing unit 65, by analysis of the map generated in the first pass and bringing into conformity parameters, visual or others, obtained in the first pass and in the second pass. This may be acheived by any of the well known techniques of image matching by correlation, as done in image analysis, or any other suitable signal analysis techniques.

As the capsule 60 moves through the digestive system (gastrointestinal tract) 62, in its first pass, it views the walls of the digestive system in the method described in FIGS. 2 and 3 and in U.S. Pat. No. 5,604,531, and transmits the resultant images to a reception system 64 typically located outside a patient. The reception system 64 receives a multiplicity of versions of the images, each version received by a different antenna (described in FIGS. 2 and 3) and either stores the received signals in the storage unit 68 or provides the received signals, directly, by IR or telephony, to the data processor 66. The data processor 66 typically operates two monitors, a position monitor 63, on which the current location of the capsule 60 within the digestive system is recorded, and, optionally, displayed and an image monitor 61, on which the image currently viewed by the capsule 60 is displayed.

The reception system 64 can either be portable, in which case, the data it receives is temporarily stored in a storage unit 68 prior to its processing in data processor 66, or it can be stationary and close to the data processor 66.

The capsule 60 location can be displayed two- or three-dimensionally on position monitor 63, typically, though not necessarily, as an overlay to a drawing of the digestive tract. The progress of capsule 60 is monitored by repeated or periodic localization of the capsule, and can be displayed on position monitor 63.

A forward filming device can be distinguished from a backwards filming device by the flow direction of the image. Information relating to the direction of the device motion enables more precise localization of the storage compartment end of the device. Furthermore, analysis of the optical flow enables to calculate the device velocity in the gastrointestinal tract.

The repeated localizations generate a map of the route taken by the capsule in the gastrointestinal tract 62. The generated map 70 is shown in FIG. 7. For maximum accuracy, images displayed on image monitor 61 are compared with the generated map 70 displayed on position monitor 63 to identify the location of a pathology 72, though, a location may be identified by analysis of parameters other than visual (such as pH, temp, etc.), which were sensed during the first pass in the gastrointestinal tract.

Upon identifying the location of a pathology 72 on the gastrointestinal tract map 70, either visually or by analysis of other sensor means input, capsule 60 is inserted into the gastrointestinal tract for a second pass. As capsule 60 moves through the digestive system 62, in its second pass, it is monitored as above. When arriving at the location of the pathology 72, or at any other point on map 70, determined as the point for advantageously releasing medicament for the treatment of the pathology, the capsule 60 is controlled to release the medicament from the medicament storage compartment of the capsule (45 in FIG. 4). The release of the medicament may be autonomous, automatically controlled by analyzing unit 65 or remotely controlled by an external operator.

It will be appreciated by persons skilled in the art that the present invention is not limited by what has been particularly shown and described herein above. Rather the scope of the invention is defined by the claims which follow:

What is claimed is:

1. A method comprising:
   recording a first set of images from a gastrointestinal tract using a swallowable imaging device;
   identifying an image showing a location of interest;
   recording a second set of images from the gastrointestinal tract using a swallowable imaging device; and
   performing image analysis by comparing images from the first set with images from the second set to identify in the second set an image of interest corresponding to an image in the fist set, thereby determining the location of the imaging device relative to the location of interest.

2. The method according to claim 1, wherein the imaging device is to generate data, and wherein the imaging device is a capsule comprising:
   means for signal analysis of data generated in a first pass and a second pass; and
   means for controlling the imaging device in a second pass according to said signal analysis; and
   means for performing a job in the gastrointestinal tract.

3. The method according to claim 1, comprising the steps of:
   inserting the imaging device into the gastrointestinal tract in a first pass;
   locating the imaging device; and
   displaying the location on a position monitor.

4. The method according to claim 3, further comprising a step of displaying the location of the imaging device two or three dimensionally.

5. The method according to claim 4, wherein the location of the imaging device is displayed as an overlay to a schematic presentation of the gastrointestinal tract.

6. The method according to claim 1, wherein the step of recording a first set of images using a swallowable imaging device comprises recording the first set of images in a first pass, and wherein the step of recording a second set of images using a swallowable imaging device comprises:
   recording the second set of images from the gastrointestinal tract in a second pass;
   performing image analysis by comparing images from the first pass and of images from in the second pass; and
   determining the location of the imaging device relative to the location of interest.

7. The method according to claim 6, wherein the first pass and the second pass are one or more passes.

8. The method according to claim 1, wherein the location of interest is a location of a pathology.

* * * * *